United States Patent
Montgomery

(10) Patent No.: US 9,775,790 B2
(45) Date of Patent: *Oct. 3, 2017

(54) METHOD AND COMPOSITIONS FOR WHITENING TEETH

(71) Applicant: ORACEUTICAL LLC, Lee, MA (US)

(72) Inventor: R. Eric Montgomery, Lee, MA (US)

(73) Assignee: Oraceutical LLC, Lee, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,851

(22) Filed: Nov. 17, 2014

(65) Prior Publication Data

US 2015/0140515 A1 May 21, 2015

Related U.S. Application Data

(63) Continuation of application No. 13/658,517, filed on Oct. 23, 2012, now Pat. No. 8,888,489.

(51) Int. Cl.
| | |
|---|---|
| A61C 19/06 | (2006.01) |
| A61C 17/00 | (2006.01) |
| A61K 8/22 | (2006.01) |
| A61N 5/06 | (2006.01) |
| A61C 13/15 | (2006.01) |
| A61K 8/81 | (2006.01) |
| A61C 11/00 | (2006.01) |

(52) U.S. Cl.
CPC .............. A61K 8/22 (2013.01); A61C 11/00 (2013.01); A61C 17/005 (2013.01); A61C 19/003 (2013.01); A61C 19/004 (2013.01); A61C 19/06 (2013.01); A61C 19/066 (2013.01); A61K 8/8152 (2013.01); A61N 5/0603 (2013.01); A61N 5/0624 (2013.01); A61K 2800/59 (2013.01); A61N 2005/0606 (2013.01); A61N 2005/0651 (2013.01); A61N 2005/0662 (2013.01)

(58) Field of Classification Search
None
See application file for complete search history.

(56) References Cited

U.S. PATENT DOCUMENTS

| | | |
|---|---|---|
| 3,235,459 A | 2/1966 | Francis |
| 3,939,599 A | 2/1976 | Henry et al. |
| 4,661,070 A | 4/1987 | Friedman |
| 4,952,143 A | 8/1990 | Becker et al. |
| 5,004,124 A | 4/1991 | Stefaniak et al. |
| 5,032,178 A | 7/1991 | Cornell |
| 5,240,415 A | 8/1993 | Haynie |
| 5,247,218 A | 9/1993 | Sven |
| 5,401,495 A | 3/1995 | Murayama |
| 5,658,148 A | 8/1997 | Neuberger et al. |
| 5,785,527 A | 7/1998 | Jensen et al. |
| 5,847,120 A | 12/1998 | Collins et al. |
| 5,853,428 A | 12/1998 | Collins et al. |
| 5,876,625 A | 3/1999 | Collins et al. |
| 5,921,251 A | 7/1999 | Joshi |
| 5,922,307 A | 7/1999 | Montgomery |
| 5,938,439 A | 8/1999 | Mertins et al. |
| 6,011,152 A | 1/2000 | Gordon-Wylie et al. |
| 6,018,840 A | 2/2000 | Guay et al. |
| 6,048,202 A | 4/2000 | Jensen et al. |
| 6,051,704 A | 4/2000 | Gordon-Wylie et al. |
| 6,054,580 A | 4/2000 | Collins et al. |
| 6,056,548 A | 5/2000 | Neuberger et al. |
| 6,099,586 A | 8/2000 | Collins et al. |
| 6,100,394 A | 8/2000 | Collins et al. |
| 6,136,223 A | 10/2000 | Collins et al. |
| 6,164,967 A | 12/2000 | Sale et al. |
| 6,174,516 B1 | 1/2001 | Curtis et al. |
| 6,241,779 B1 | 6/2001 | Collins et al. |
| 6,331,291 B1 | 12/2001 | Glace et al. |
| 6,397,424 B1 | 6/2002 | Leung |
| 6,521,215 B2 | 2/2003 | Okay |
| 6,599,126 B1 | 7/2003 | Sale et al. |
| 6,602,073 B2 | 8/2003 | Schilling et al. |
| 6,611,110 B1 | 8/2003 | Fregoso |
| 6,623,272 B2 | 9/2003 | Clemans |
| 6,759,030 B2 | 7/2004 | Kosti |
| 6,792,640 B2 | 9/2004 | Lev |

(Continued)

FOREIGN PATENT DOCUMENTS

| | | |
|---|---|---|
| CN | 1863519 | 11/2006 |
| EP | 1262172 | 12/2002 |

(Continued)

OTHER PUBLICATIONS

Official letter dated Apr. 7, 2014, in EP 13 192 958.0.
Applicant's letter dated Nov. 13, 2014, in EP 13 192 958.0.
Written Opinion with International Search Report dated Feb. 9, 2015, in PCT/EP2014/074549.
Paris et al., "Penetration Coefficients of Commercially Available and Experimental Composites Intended to Infiltrate Enamel Carious Lesions", Dental Materials 23 (2007), pp. 742-748.
Cadenaro et al., "Influence of Whitening on the Degree of Conversion of Dental Adhesives on Dentin," Eur. J. Oral Sci., vol. 114 (2006), pp. 257-262.
Kugel et al., "Composites and Whitening: How and When to Combine Treatments," http://www.dentalaegis.com/special-issues/2007/03/composites-and-whitening-how-and-when-to-combine-treatments (last visited Jul. 19, 2013).

(Continued)

*Primary Examiner* — Tigabu Kassa
(74) *Attorney, Agent, or Firm* — David M. Quinlan, P.C.

(57) ABSTRACT

A tooth whitening method applies a light transmitting oxidizing composition to teeth in an oral cavity, after which a hand-held LED light source with a light transmitting lens and a cup forming a chamber having an open end is moved over the teeth so that the cup distributes the oxidizing composition while the teeth are exposed to light transmitted through the lens. This not only ensures intimate contact of the teeth with the oxidizing composition, but also maintains a more or less constant spacing between the light source and the tooth surfaces for optimum results. A sealant is then applied to the teeth to resist moisture contamination of the oxidizing composition.

21 Claims, 1 Drawing Sheet

(56) References Cited

U.S. PATENT DOCUMENTS

| | | |
|---|---|---|
| 6,800,671 B1 | 10/2004 | Montgomery |
| 6,902,397 B2 | 6/2005 | Farrell et al. |
| 7,060,818 B2 | 6/2006 | Horwitz et al. |
| 7,354,448 B2 | 4/2008 | Altshuler et al. |
| 7,581,864 B2 | 9/2009 | Craig |
| 8,002,546 B2 | 8/2011 | Viscomi |
| 8,033,746 B2 | 10/2011 | Tsai |
| 8,177,450 B2 | 5/2012 | Zhang |
| 8,214,958 B2 | 7/2012 | Pinyayev et al. |
| 8,481,678 B2 | 7/2013 | Anton et al. |
| 8,888,489 B2 | 11/2014 | Montgomery |
| 9,101,438 B2 | 8/2015 | Montgomery |
| 2001/0046477 A1 | 11/2001 | Wolfe |
| 2002/0006422 A1 | 1/2002 | Koda et al. |
| 2002/0197214 A1 | 12/2002 | Bublewitz et al. |
| 2003/0171702 A1 | 9/2003 | Thompson et al. |
| 2003/0198605 A1* | 10/2003 | Montgomery ............ A61O 5/00 424/53 |
| 2004/0019990 A1 | 2/2004 | Farrell et al. |
| 2004/0033205 A1 | 2/2004 | Date et al. |
| 2004/0057910 A1 | 3/2004 | Lee et al. |
| 2004/0063075 A1 | 4/2004 | Karazivan |
| 2004/0105834 A1 | 6/2004 | Singh et al. |
| 2004/0241110 A1 | 12/2004 | Lee |
| 2004/0241620 A1 | 12/2004 | Allred et al. |
| 2005/0026103 A1 | 2/2005 | Wasylucha |
| 2005/0026107 A1 | 2/2005 | Mongtomery |
| 2005/0084826 A1 | 4/2005 | Pilaro et al. |
| 2005/0100514 A1 | 5/2005 | Sakaguchi et al. |
| 2005/0113510 A1* | 5/2005 | Feldstein ............ A61K 8/042 524/556 |
| 2005/0175956 A1 | 8/2005 | Russell et al. |
| 2005/0220724 A1 | 10/2005 | Busch et al. |
| 2005/0249677 A1 | 11/2005 | Malcmacher et al. |
| 2005/0260142 A1 | 11/2005 | Philp et al. |
| 2006/0034780 A1 | 2/2006 | Guan et al. |
| 2006/0047329 A1 | 3/2006 | Krespi et al. |
| 2006/0105292 A1 | 5/2006 | Dorsey et al. |
| 2006/0171905 A1 | 8/2006 | Allred |
| 2006/0183081 A1 | 8/2006 | Bevilacqua et al. |
| 2006/0198795 A1 | 9/2006 | Giniger |
| 2006/0198797 A1 | 9/2006 | Giniger |
| 2006/0223024 A1 | 10/2006 | Hochman |
| 2006/0240386 A1 | 10/2006 | Yaniv et al. |
| 2006/0264532 A1 | 11/2006 | Meyer-Luckel et al. |
| 2007/0092455 A1 | 4/2007 | Harwood |
| 2007/0098483 A1 | 5/2007 | Milesi et al. |
| 2007/0105063 A1 | 5/2007 | Pinyayev et al. |
| 2007/0160958 A1 | 7/2007 | Belikov et al. |
| 2007/0237727 A1 | 10/2007 | Matthews |
| 2007/0271714 A1 | 11/2007 | Adam et al. |
| 2007/0298369 A1 | 12/2007 | Rizoiu et al. |
| 2008/0057463 A1 | 3/2008 | Wong et al. |
| 2008/0060148 A1 | 3/2008 | Pinyayev |
| 2008/0131834 A1 | 6/2008 | Shepherd et al. |
| 2008/0176183 A1 | 7/2008 | Gatzemeyer et al. |
| 2008/0206706 A1 | 8/2008 | Mossle |
| 2008/0213731 A1 | 9/2008 | Fishburne |
| 2008/0255549 A1 | 10/2008 | Rose et al. |
| 2008/0256729 A1 | 10/2008 | Link |
| 2008/0274066 A1 | 11/2008 | Montgomery |
| 2008/0274442 A1 | 11/2008 | Klee et al. |
| 2008/0286713 A1 | 11/2008 | Nanda |
| 2009/0081605 A1 | 3/2009 | Hay et al. |
| 2009/0092563 A1 | 4/2009 | Allred et al. |
| 2009/0271936 A1 | 11/2009 | Walanski et al. |
| 2011/0009834 A1 | 1/2011 | Asmussen et al. |
| 2011/0070560 A1 | 3/2011 | Hertz |
| 2011/0123958 A1 | 5/2011 | Piergallini et al. |
| 2011/0144410 A1 | 6/2011 | Kennedy |
| 2011/0256501 A1 | 10/2011 | Lampert |
| 2012/0258418 A1 | 10/2012 | Shen |
| 2013/0164710 A1 | 6/2013 | Montgomery |
| 2014/0113253 A1 | 4/2014 | Montgomery |
| 2015/0064645 A1 | 3/2015 | Jablow et al. |

FOREIGN PATENT DOCUMENTS

| | | |
|---|---|---|
| WO | 0226196 | 4/2002 |
| WO | 2004028497 | 4/2004 |
| WO | 2004103303 | 12/2004 |
| WO | 2005041911 | 5/2005 |
| WO | 2005072692 | 8/2005 |
| WO | 2011133793 | 10/2011 |
| WO | 2013128328 | 9/2013 |
| WO | 2015071386 | 5/2015 |

OTHER PUBLICATIONS

International Preliminary Report on Patentability and Written Opinion in PCT/US2011/033464, Aug. 15, 2013.

Official letter dated Jan. 4, 2016, in Chinese appln. No. 2011/800303719 (with translation).

International Preliminary Report on Patentability and Written Opinion in PCT/US2016/046103, Oct. 30, 2016.

* cited by examiner

METHOD AND COMPOSITIONS FOR WHITENING TEETH

BACKGROUND OF THE INVENTION

As the connections between healthy teeth and gums, and general overall health, have become increasingly evident in the past 100 years, oral care has become an important part of people's daily health maintenance regimens. In the process, a healthy looking smile has become representative of one's level of personal grooming, and even social status, with straight, white and well shaped teeth being promoted in advertising and by cosmetic dentists as an integral part of one's self-image. Over the past 20 years, the availability of tooth whitening products and services has exploded in the marketplace, ranging from low priced over-the-counter (OTC) self-applied trays, strips, pens, mouthwashes and toothpastes, to expensive professionally applied or monitored products and procedures capable of effectively whitening teeth in as little as 45 minutes. In general, professionally applied products and services administered to a patient in a dental office or other clinical setting are seen to achieve the best teeth whitening results in the shortest amount of time. This is primarily due to the concentration of active ingredient, usually hydrogen peroxide or a hydrogen peroxide precursor, found in professionally applied whitening compositions. Such high concentrations, typically above 15% hydrogen peroxide by weight and often as high as 50% hydrogen peroxide by weight, can only be safely administered in a controlled setting where a professionally trained individual can isolate soft tissues from contact with these highly oxidative compositions. Frequent monitoring, of a patient's progress over, for instance, a one-hour period is also critical in maintaining a high degree of safety when working with such high hydrogen peroxide concentrations. Optionally, light or heat energy may be applied in conjunction with these strong oxidizing compositions, in order to accelerate the process beyond that which is possible using just the compositions on then own. In general, these professionally-monitored products and services applied in a dental office or clinic will be referred to collectively as in-office or chairside whitening procedures.

Chairside whitening procedures are generally performed during a dental appointment scheduled specifically for the purpose of whitening the patient's teeth, or as an adjunct following a professional teeth cleaning, formally known as a dental prophylaxis or "prophy". When tooth whitening is conducted immediately following a prophy, the total amount of time that the patient must remain in a dental chair can often exceed two hours.

A professional tooth cleaning is recommended by the American Dental Association as a means to prevent gum disease. Gum disease, of periodontitis, is the primary cause of tooth loss in adults over the age of 40. Gum disease has also been linked to other health problems, such as heart disease, osteoporosis, respiratory diseases, and other more serious systemic diseases. According to the Center for Disease Control and Prevention, approximately 68% of adults in the United States have at least one professional tooth cleaning annually (2008). There is speculation as to the reasons why so many adults neglect the benefits obtainable from regular tooth cleanings, ranging from lack of health insurance to the fear of dental procedures. Lack of patient knowledge is a problem that can be managed, however studies have shown that better education of patients only leads to modest changes in behavior and attitudes towards preventative dentistry.

In general, a typical teeth cleaning dental appointment comprises the following, procedural steps:

(1) A dental hygienist or dental assistant may or may not take x-rays of a patient's teeth.
(2) The dental hygienist or dental assistant will generally take between 15 and 60 minutes to work on the teeth and gums (the exact time depending upon both the amount of accumulation present, as well as the teeth cleaning method chosen), using a variety of tools, including manual or ultrasonic scalers to remove the tartar and plaque from the patient's teeth.
(3) The hygienist will then floss between the teeth and generally complete the cleaning procedure by polishing the front (buccal) and had (lingual) surfaces of the teeth with an abrasive composition known as a prophylaxis ("prophy") paste. Tooth polishing leaves a smooth tooth surface that is more resistant to the adhesion and buildup of dental plaque between dental cleaning appointments.

Despite the apparent benefits of preventative teeth cleaning as described above, nearly 80% of the population has some form of gum disease ranging from early stage gingivitis to advanced periodontitis. Symptoms of guru disease may include one or more of the following: bleeding gums, halitosis bad breath), bad taste in the mouth, tooth sensitivity, sore gums, loose adult teeth, abscessed teeth or gums pulling away from the teeth, changes in the way the teeth fit together or dentures fitting poorly, exudates between the gums and teeth, sores in the mouth, and actual tooth loss. Such a high rate of chronic or acute gum disease indicates a low level of compliance when it comes to scheduling of a regular dental cleaning, and any means of increasing such compliance would clearly be beneficial to the patient's general oral health.

BRIEF DESCRIPTION OF THE INVENTION

The inventive tooth cleaning and whitening method comprises novel compositions and procedural steps that allow for the simultaneous performance of a dental prophylaxis and tooth whitening procedure. The procedure involves steps performed at least partially in parallel or contemporaneously with a typical dental prophylaxi procedure during which a significant amount of plaque, tartar and acquired pellicle are removed, in general, these steps may include, but are not limited to, chemical, mechanical and/or chemomechanical tooth surface conditioning, contact or impregnation of one or more teeth with a catalyst, contact or impregnation of one or more teeth with an oxidiz ing agent, exposure of one or more teeth to actinic energy comprising heat, light, sound, ultrasound, air or mechanical pressure (and combinations thereof), and contact or impregnation of one or more teeth with a tooth remineralizing, opacifying or pigmenting composition. Combinations of the above procedural steps have been developed that accomplish significant whitening of stained teeth in less than about 90 minutes when performed in conjunction with or during a dental prophylaxis procedure.

The ability of the inventive compositions and methods to simultaneously whiten teeth in parallel with a dental cleaning procedure is highly dependent upon the ability of the oxidizing agent to penetrate into tooth enamel and dentin. Both tooth enamel and dentin are composite structures comprising both organic and inorganic phases as well as interstitial spaces that are occupied by fluid. These interstitial spaces can accommodate fluid movement, which is generally in an outward direction, in other words from the interior of the tooth towards the enamel surface. However, fluids and other materials in contact with the enamel surface can influence fluid movement through tooth enamel and dentin with concentration gradients and/or capillary action, as well as in conjunction with pressure, heat, light and other external physical forces that can change the dynamic relationship between the tooth and the fluid in contact with the tooth.

Mathematical models have been constructed to predict the ability of fluids to penetrate into porous substrates. The Lucas-Washburn equation is one such method of developing a comparative "Penetration Coefficient" for various fluids, based on their viscosity, surface tension (with air) and contact angle (with a porous substrate). The model assumes that the porous solid is a bundle of open capillaries, so in other words the Penetration Coefficient is a comparative predictor of capillary flow rate. The Lucas-Washburn equation $$d^2 = \left(\frac{\gamma \cos\theta}{2\eta}\right) rt$$

predicts the distance (d) traveled by a liquid in a porous substrate, where the liquid has a surface tension ($\gamma$) with air, a contact angle ($\theta$) with the porous substrate surface and a dynamic viscosity ($\eta$) and where (r) is the capillary pore radius and (t) is the penetration time. The bracketed component of the Lucas-Washburn equation is the Penetration Coefficient, expressed as centimeters per second $$PC = \frac{\gamma \cos\theta}{2\eta}$$

The Lucas-Washburn equation predicts that the higher the PC, the faster a liquid will penetrate into a given porous capillary substrate. This means that, at least in theory, a high PC can be achieved for liquids with low viscosities, particularly for compositions also having a low contact angle (which is often, but not always, associated with a liquid having a low surface tension that will lead to efficient wetting of the porous substrate.

Penetration coefficients have been used recently to design improved dental materials, specifically sealants and low-viscosity composites intended to arrest the progression of carious lesions (Paris, et al, *Penetration Coefficients of Commercially Available and Experimental Composites Intended to Infiltrate Enamel Carions Lesions*, Dental Materials 23 (2007) 742-748). The authors show that low viscosity materials with high Penetration Coefficients (>50 cm/s) are capable of penetrating enamel carious lesions better than materials with low PCs (see corresponding patent application US 2006/0264532).

Prior art tooth whitening compositions have generally been formulated to have high viscosities for better retention in dental trays during the bleaching process, which prevents migration of the whitening composition from the tray due to salivary dilution. Moderate to high viscosities have also been the norm for chairside whitening procedures, in order to prevent the whitening composition from migrating away from the tooth enamel surface. According to the Lucas-Washburn equation, moderate to high viscosity tooth whitening compositions (greater than about 100 centipoise at 25 deg C.) will have low Penetration Coefficients and thus be predicted to have restricted movement into the whitening target, that is, the porous enamel substrate. It would thus be advantageous to design a tooth whitening carrier composition comprising an oxidizing agent with a low viscosity (<100 cps) and a high Penetration Coefficient ( 50 cm/s) in order to achieve rapid penetration into tooth enamel and dentin.

Other factors affecting, the ability of a liquid penetrant to infiltrate enamel and dentin are (1) surface charge effects (which is related to pH of the micro environment within the tooth, as well as the PH and counter ion content of the liquid penetrant), (2) adhesion of the liquid penetrant to the tooth surface (which is related to the surface tension and wetting, ability of the liquid penetrant), and (3) osmotic effects (which are related to the direction of diffusion of the interstitial fluid in the tooth structure in relation to the liquid penetrant in contact with the tooth). Under certain circumstances, tooth whitening composition having viscosities in excess of 100 cps are contemplated, for instance when auxiliary means of increasing the penetration rate are available. For example, a tooth whitening composition with a viscosity between 5,000 and 100,000 cps can be utilized if heat and/or light and/or vibrational energy is used to increase the penetration rate of the composition into the tooth enamel structure.

In general, one aspect of the inventive simultaneous tooth cleaning and whitening method comprises the following steps, preferably performed in a sequence of steps comprising:

applying an oxidizing composition to the surfaces of the teeth to be whitened; and
performing a dental cleaning or hygiene procedure while the oxidizing composition is in contact with the teeth to be whitened.

In another aspect of the invention a method for simultaneously cleaning and whitening teeth comprises the steps of:
applying a conditioning composition to the teeth surface;
applying an oxidizing composition to the teeth surface;
applying a sealant composition to the teeth surface;
cleaning the teeth surface;
polishing the teeth surface; and
removing the condition compositions from the teeth.

In yet another aspect of the invention, a method for simultaneously cleaning and whitening teeth comprises the steps of:
applying a composition to the teeth surface, wherein said composition is comprised of at least a fluid carrier, a tooth conditioner, an oxidizing agent and a water-resistant polymer,
cleaning said teeth surface;
polishing said teeth surface; and
removing said composition, There is typically an extensive amount of scraping, scaling, and other modes of plaque and tartar removal performed during a dental cleaning or prophylaxis. During the cleaning procedure, the patient's mouth is usually open for an extended period of time during which excess saliva may accumulate in the oral cavity and come in contact with the tooth surfaces. Also, the patient is typically asked to rinse with water or a mouthwash at various times during the cleaning procedure in order to clear debris (plaque, tartar, blood, saliva, etc) from the oral cavity that accumulates from the cleaning process. It has been found that in order to achieve a desirable (that is, a noticeable) level of tooth whitening during said dental cleaning, or prophylaxis, it is advantageous to prevent moisture from saliva or external sources (such as the rinsing solutions referred to above) from directly contacting the tooth surfaces that have been previously contacted with the oxidizing composition. By creating a barrier between extraneous moisture and the oxidizing composition, said moisture is prevented or limited in its ability to remove, dilute, neutralize or otherwise decrease the effectiveness of the oxidizing composition during the cleaning procedure.

One means of limiting the contact of external moisture with the oxidizing composition is to utilize an oxidizing composition having hydrophobic ("water-repelling") properties when in contact with the tooth surface.

An alternative means of preventing moisture contamination of the oxidizing composition on the tooth surface is to cover the oxidizing composition with a film of water-insoluble or water-resistance material. Such materials may include, but are not limited to polymer films and water-resistant or water-insoluble fluids, gels, creams, waxes and solids.

Yet another alternative means of preventing moisture contamination of the oxidizing composition on the tooth surface is to cover the oxidizing composition with a curable composition that can be converted from a liquid or gel into a higher viscosity liquid, gel or solid upon exposure to an external source of energy. Said external energy source may be electromagnetic or light energy, sound or ultrasound energy, mechanical or vibrational energy, electrical energy, or combinations thereof.

A preferred tooth cleaning and whitening method comprises the following steps
1) Placing a cheek and lip retraction means into the oral cavity of a subject. Said means may include a cheek retractor and/or cotton rolls placed in such a way as to prevent the soft tissue of the inside of the lips and cheeks from coming into contact with the tooth surfaces,
2) Conditioning of the teeth surfaces to be whitened with a conditioning agent or conditioning composition, using chemical, mechanical, or chemo-mechanical means,
3) Contacting the conditioned tooth surfaces with one or more compositions comprising an oxidizing agent,
4) Contacting the tooth surfaces with a water-resistant coating or film-forming composition to protect the oxidizing agent from direct contact with external moisture during the tooth cleaning process,
5) Cleaning and scaling of subject's teeth in proximity to the gum line, gingival margins and crevicular spaces while the compositions of steps (3) and (4) above are in contact with the tooth surfaces,
6) Polishing, the teeth with prophylaxis or polishing paste following completion of step (5),
7) Optionally repeating steps (3) and (4), and
8) Cleaning and rinsing all residual materials from tooth and gum surfaces that were applied or produced during the performance of steps (1) through (7).

Modifications to the above procedure are possible and are some cases preferable. For instance, the conditioning agent or conditioning composition may be combined with the oxidizing composition of step (3) in order to reduce the amount of time required to perform the combined cleaning and whitening procedure. Also, water-resistant properties may be imparted to the oxidizing composition of step (3) in order to obviate the need for a separate step (4). Therefore, it is contemplated, but not required, that the compositions and/or agents of steps (2), (3) and (4) may be combined into a single composition (a) prior to packaging, (b) just prior to use, or (c) on the tooth surface during use. Optionally, a tooth-desensitizing agent, such as potassium nitrate, may be applied before, during, or after any of the steps outlined above. Such tooth-desensitizing, agent may be applied as a stand-alone formulation or combined with the conditioning agent, oxidizing agent, water-resistant or film-forming composition, or any combination of these.

It is also contemplated within the scope of this invention to employ light energy and/or heat energy to accelerate the tooth whitening process through various means such as increasing the rate of oxidizing composition penetration into enamel and dentin, increasing the susceptibility of tooth stain chromogens to oxidation, and accelerating the oxidation process through advanced oxidation processes such as the photo-Fenton reaction. An added benefit of employing light energy, particularly that in the blue region of the light spectrum (approximately 400-500 nanometers), during the inventive simultaneous tooth cleaning and whitening process, is observed by the attenuation and/or killing of periodontal pathogens within the light energy exposure field. A particularly useful benefit to reducing the viability of periodontal pathogens prior to, during and/or after a tooth cleaning is the reduction in risk associated with a lower bacterial burden during a moderately invasive procedure (tooth cleaning) that can sometimes involve bleeding. Reduction of the available numbers and types of oral pathogens during a tooth cleaning, process may be of significant benefit to the subject's overall oral and whole body health, since the association between the presence of periodontal pathogens, such as the black pigmented bacteria species *Fusobacterium nucleatum* and *Porphyromonas gingivalis*, and the incidence of systemic diseases (such as heart disease) has been shown in recent years to be quite strong. Light energy employed in the initial steps of the present inventive method is seen to be most beneficial, since pathogen reduction prior to the invasive cleaning process would occur. However, light energy applied at any point in time during the cleaning and whitening process can be of significant benefit to the patient's gingival and periodontal health.

Particularly useful is light energy having the following characteristics: wavelengths of between 380 and 700 nanometers (nm), between 400 and 500 nm, and between 410 and 460 nm; and light intensity (measured at the target surface, for example the tooth or gum surfaces, in terms of power density) of between 100 and 5,000 milliwatts per centimeter squared ($mW/cm^2$), between 100 and 2,000 $mW/cm^2$, between 500 and 1,500 $mW/cm^2$, and between 100 and 300 $mW/cm^2$. Light sources such as light emitting diodes (LEDs), quartz halogen bulbs, tungsten halogen bulbs, plasma arc bulbs, and xenon flash lamps, to name a few, are contemplated to have utility in the present invention. Preferred light sources are LEDs with emission peaks between 400 and 500 nanometers.

BRIEF DESCRIPTION OF THE DRAWING

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

Figure 1:
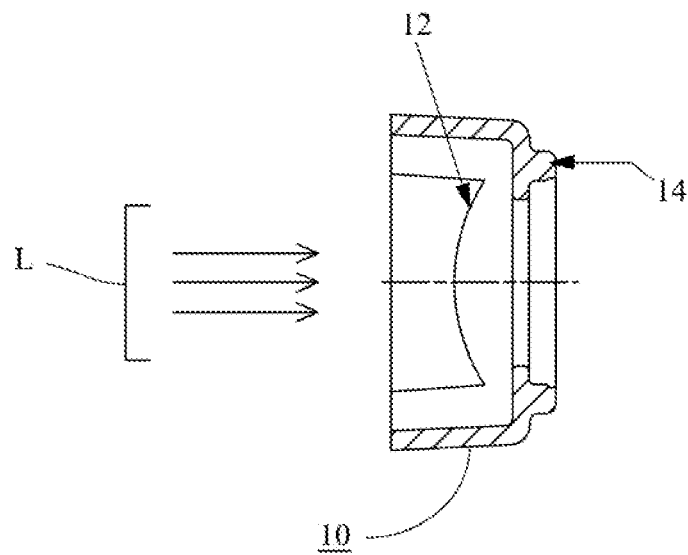
FIG. 1 is a schematic depiction of an over molded lens that can be attached to a hand-held dental curing lamp for enhancing whitening, in accordance with one aspect of the present invention.

Those skilled in the art will readily understand that the drawings in some instances may not be strictly to scale and that they may further be schematic in nature, but nevertheless will find them sufficient, when taken with the detailed descriptions of preferred embodiments that follow, to make and use the present invention.

DETAILED DESCRIPTION OF PREFERRED EMBODIMENTS

The compositions of the present invention are designed to provide a fast and effective means of whitening the teeth during the performance of a dental cleaning or prophylaxis. Various combinations of tooth conditioning compositions, oxidizing compositions and sealant compositions are envisaged to have utility in the practice of the inventive method, and the properties of these individual compositions may be combined into a single composition for ease of use and application. Alternatively, a tooth conditioning function may be combined with an oxidizing function into a single composition. Another alternative is to combine a tooth sealing function with an oxidizing function to reduce the number of application steps.

The tooth conditioning composition may comprise a fluid carrier and one or more tooth conditioning ingredients. Fluid carriers include water, ethanol, diethyl ether, methoxypropane(methyl propyl ether), dimethyl isosorbide and combinations thereof. The tooth conditioning function, that is the ingredient or ingredients that remove the acquired pellicle and subsequently open the enamel porosities for better penetration of the oxidizing composition, may be provided by ingredients having an acidic and/or calcium chelating capabilities. Useful acidic compounds include both inorganic and organic acids such as phosphoric acid, hydrochloric acid, acetic acid, lactic acid, citric acid, and their salts. Useful calcium chelating compounds include both inorganic and organic chelating agents such as ethylenediaminetetraacetic acid (EDTA), phytic acid, 1-hydroxyethylidene-1, 1'-diphosphonic acid, citric acid, and their salts. The tooth conditioning composition may also comprise a colorants and/or pigments to assist in the placement and application of the tooth conditioning composition onto the teeth during the combination whitening and cleaning procedure.

The oxidizing composition comprises a fluid carrier and an oxidizing, agent. Fluid carriers include water, ethanol, diethyl ether, methoxypropane(methyl propyl ether), dimethyl isosorbide and combinations thereof. Oxidizing agents include peroxides, metal chlorites, percarbonates, perborates, peroxyacids, hypochlorites and combinations thereof. Preferred oxidizing agents are hydrogen peroxide, carbamide peroxide, poly(vinyl pyrrolidone)-hydrogen peroxide complex (Peroxydone®, ISP Corp, Wayne, N.J.), peroxyacetic acid, and sodium chlorite. The oxidizing composition preferably has a viscosity of less than about 100 centipoise and most preferably less than about 10 centipoise. The oxidizing composition may also comprise active components further related to the tooth whitening function (such as stabilizers, a secondary oxidizing agent, an oxidation catalyst, a pH-adjusting agent, and a calcium cheating agent), or to a non-tooth whitening function (such as remineralization of the tooth surface, prevention of tooth decay, tooth-desensitization, prevention of gingivitis and/or periodontal disease, and other diseases or conditions of the oral cavity). In addition, the oxidizing composition may comprise one or more colorants and/or pigments to assist in the placement and application of the sealant onto the teeth during the combination whitening and cleaning procedure. Such colorants and/or pigments may also be present to provide a stain masking effect that changes the appearance of the tooth while the oxidizing composition is in contact with the tooth surface during the procedure.

Preferred oxidation catalysts are chelated metal complexes, in particular complexes of iron and manganese. Particularly preferred chelated metal complexes are the family of tetraamido-N-macrocyclic ligand (TAML) iron catalysts described in U.S. Pat. Nos. 7,060,818, 6,241,779, 6,136,223, 6,100,394, 6,054,580, 6,099,586, 6,051,704, 6,011,152, 5,876,625, 5,853,428, and 5,847,120.

The oxidizing compositions of the present invention ay also contain a surface active agent in order to lower the surface tension of the composition to provide for better wetting and adhesion of the liquid to the surface of the tooth. Anionic, cationic, non-ionic and zwitterionic surfactants are contemplated to have utility in providing the oxidizing compositions with a low surface tension. Preferred surfactants are sulfobetaines (such as amidosulfobetaine 3-16 and Lonzaine CS) and fluorosurfactants (such as Capstone 50 and Capstone FS-10).

Sealant compositions of the present invention may comprise a water-resistant polymer, copolymer or crosspolymer, and a fluid carrier. Hereinafter the term "polymer" and "polymers" shall he used to denote polymer(s), copolymer(s) or crosspolymer(s). Suitable water-resistant polymers include acrylate polymers, methacrylate polymers, modified cellulosic polymers, silicone polymers, urethane polymers, polyamide polymers, vinyl polymers, vinyl pyrrolidone polymers, maleic acid or itaconic acid polymers, and others. The water-resistant polymer should be soluble or dispersible in the fluid carrier. Particularly preferred polymers are poly(butyl methacrylate-co-(2-dimethylaminoethyl)methacrylate-co-methyl methacrylate), poly(ethyl acrylate-co-methyl methacrylate-co-trimethylammonioethyl methacrylate chloride), ethylcellulose, and esterified or crosslinked poly(methyl vinyl ether-co-maleic anhydride). The fluid carrier may be a volatile solvent which will evaporate after contacting the sealant composition with the tooth surface, leaving behind a liquid or solid coating or film. Said solvent should have an evaporation rate equal to or greater than that of water, and preferably equal to or greater than that of butyl acetate. Suitable solvents include, but are not limited to, water, ethanol, diethyl ether, methoxypropane(methyl propyl ether), acetone, ethyl acetate, and other highly volatile solvents.

Alternatively, the sealant compositions may be curable liquids or gels, which are placed or the tooth surface and subsequently exposed to sonic form of activating energy which converts the liquid or gel sealant composition to a solid coating or film. Curable sealant compositions may also be chemically cured, whereby two or more components are combined just prior to use and placed on the tooth surface to cure, in other words, to change from a liquid or gel into a solid coating or film.

The sealant composition may also comprise active components related to a tooth whitening function (such as an oxidizing agent, an oxidation catalyst, a pH-adjusting agent, and a calcium chelating agent), or to a non-tooth whitening function (such as remineralization of the tooth surface, tooth-desensitization, prevention of tooth decay, prevention of gingivitis and/or periodontal disease, and other diseases or conditions of the oral cavity). In addition, the sealant composition may comprise one or more colorants and/or pigments to assist in the placement and application of the sealant onto the teeth during the combination whitening and cleaning procedure. Such colorants and/or pigments may also be present to provide a stain masking effect that changes the appearance of the tooth while the sealant composition is attached to the tooth surface in the form of a coating or film.

The combination whitening and cleaning method described herein may also be practiced by employing an additional source of energy to accelerate the oxidation process and further reduce the time needed to complete the procedure. External energy sources such as electromagnetic or light energy, sound or ultrasound energy, mechanical or vibrational energy, electrical energy, or combinations thereof may be advantageously employed at any point in time during the combination whitening and cleaning procedure to accelerate the process.

EXAMPLES

In order to achieve a significant degree of tooth whitening in an abbreviated time frame suitable for integration into the tooth cleaning (dental prophylaxis) process, ideal conditions for (1) oxidizer penetration into the tooth and (2) conversion of initial oxidizer form into active whitening species must be facilitated.

Time limitations are imposed on the additional steps required to achieve whitening during the tooth cleaning process by the realities of patient scheduling in the typical dental office, and such additional steps should not exceed 30 minutes beyond or in addition to the time required to perform a typical dental prophylaxis. Optimal conditions for penetration of an active whitening composition into tooth enamel must he present in order to reduce the amount of time and oxidizer concentration required to reach intrinsic stain depth. Important factors related to oxidizer penetration into the tooth are (1) the viscosity of the oxidizing composition, (2) the surface tension of the oxidizing composition and (3) the surface free energy (also called the critical surface tension) of the tooth surface.

The surface free energy of exposed tooth enamel is generally in the range of about 50-55 dynes/cm, however the acquired pellicle can lower this number significantly. In fact, one of the important functions of the acquired pellicle is to reduce the critical surface tension of the tooth surface in order to reduce the adhesion of bacteria. Liquid and gel compositions contacting the tooth surface penetrate into the tooth structure in relation to four primary factors: time, viscosity of the liquid or gel, surface tension of the liquid or gel, and surface free energy of the tooth at the point of contact.

The relationship of liquid surface tension to solid surface free energy, low contact angle (the tangential angle formed by a droplet deposited on a solid surface) and low viscosity are all directly related to the Penetration Coefficient (as derived from the Lucas-Washburn equation) and must be optimized for the whitening composition to (1) rapidly wet the surface of tooth enamel and (2) penetrate the available porosities and channels through enamel as quickly as physically possible.

Example 1

The ability of various oxidizing compositions to penetrate intact enamel and dentin was determined as follows. Extracted molar and pre-molar teeth were obtained from orthodontists with patient consent and stored refrigerated in phosphate buffered saline (PBS) solution at 6.8 until use. In order to assess the ability of various liquid carrier fluids to penetrate tooth enamel, teeth were sectioned to remove their roots and a 3 mm diameter chamber was created in the center of the sectioned crown that was filled with PBS solution. The crowns were partially immersed (chamber with PBS solution facing up) in various liquid carrier fluids and a small (1 microliter) sample of the PBS solution was drawn every 60 seconds and place on a peroxide test strip (EM Quant Strips 10337, EMD Chemicals, a division of Merck SA, Darmstadt, Germany) to determine the amount of time required for hydrogen peroxide to penetrate the tooth enamel and dentin from the outer surface of the crown to the interior chamber containing PBS.

Oxidizing compositions in Table 1 below were prepared and stored in 20 ml glass vials until use.

TABLE 1

| Ingredient | Percent (w/w) | | | | | | | | | | | |
| --- | --- | --- | --- | --- | --- | --- | --- | --- | --- | --- | --- | --- |
| | 1A | 1B | 1C | 1D | 1E | 1F | 1G | 1H | 1I | 1J | 1K | 1L |
| Water | 75.0 | 65.0 | 75.0 | 65.0 | 85.0 | 75.0 | 65.0 | 75.0 | 65.0 | 75.0 | 65.0 | 100.0 |
| Ethanol 200 | 10.0 | 20.0 | 5.0 | 15.0 | | 5.0 | 15.0 | | | | | |
| Diethyl ether | | | 5.0 | 5.0 | | | | | | | | |
| Methoxypropane | | | | | | 5.0 | 5.0 | | | | | |
| Acetone | | | | | | | | 10.0 | 20.0 | | | |
| Dimethyl isosorbide | | | | | | | | | | 10.0 | 20.0 | |
| Hydrogen peroxide | 15.0 | 15.0 | 15.0 | 15.0 | 15.0 | 15.0 | 15.0 | 15.0 | 15.0 | 15.0 | 15.0 | 0.0 |
| Adjusted to pH 4.0 with potassium hydroxide 0.1M | | | | | | | | | | | | |
| Viscosity (cps @ 25 C.) | <1 | <1 | <1 | <1 | 1.3 | <1 | <1 | <1 | <1 | 1.5 | 1.5 | 1 |
| Surface tension dynes/cm | <40 | <40 | <40 | <40 | >50 | <40 | <40 | <40 | <40 | <40 | <40 | >50 |
| Contact angle (deg) | <10 | <10 | <10 | <10 | 30+ | <10 | <10 | <10 | <10 | 15 | 15 | 50+ |
| PC (calculated) | >100 | >100 | >100 | >100 | <50 | >100 | >100 | >100 | >100 | >100 | >100 | <30 |
| $H_2O_2$ detection (min) | 13 | 12 | 12 | 10 | 20 | 14 | 12 | 14 | 14 | 15 | 15 | ND* |

*ND = Not detected

Oxidizing compositions in Table I trended towards faster penetration of the tooth when both contact angle and viscosity of the composition was low (Examples 1A, 1B, 1C, 1D, 1F, 1G, 1H, 1I, 1J, and 1K). Oxidizing with high contact angles (greater than 30 degrees) did not seem to penetrate as well as those with contact angles less than about 10 degrees.

Example 2

The following multi-step process was developed to provide for rapid and effective whitening of the teeth during a dental cleaning procedure.

Step 1—Acquired Pellicle Removal

Facilitating oxidizer penetration into the tooth requires a thorough removal or modification of the acquired pellicle prior to contact with the oxidizer formulation. Therefore, whether integrated into a dental prophylaxis procedure or performed as a stand-alone process, the first step in the abbreviated whitening process (after determining a starting tooth shade) must be the removal of the acquired pellicle using chemical, mechanical or (preferably) chemo-mechanical means. Once the acquired pellicle has been removed, it is important that the "cleaned" tooth enamel surface has limited contact with the patient's saliva prior to application of the oxidizer composition (see Step 2) in order to prevent reformation of the pellicle film on the exposed enamel surface. Removal or modification of the acquired pellicle and optional micro-roughening of the exposed enamel surface will elevate the enamel surface free energy (preferably above about 60 dyne/cm) which promotes better wetting of the enamel surface by the oxidizing composition. Surface wetting is a key factor related to the speed at which a composition penetrates enamel, analogous to the effects of viscosity and surface tension on the penetration of bonding adhesives into conditioned enamel and sealants into caries lesions.

Step 1a Placement of Cheek Retractor or Other Means of Preventing Contact of the Lips and Interior Mini Surfaces with the Teeth.

Step 1b Application of Conditioner for 30-60 Seconds

Tooth Conditioner Composition

| Ingredient | Percent (w/w) |
| --- | --- |
| Water | 90.0 |
| Poly (methyl vinyl ether-co-maleic anhydride)* | 10.0 |

*Gantrez S-95 (ISP Corp, Wayne, NJ) (hydrolyzed, pH 2.0)

Step 2—Oxidizer Contact and Penetration

Once the acquired pellicle has been removed, the teeth surfaces are contacted with a low viscosity oxidizer composition with a surface tension significantly lower than that of the surface free energy of the exposed enamel surface. A low viscosity oxidizing composition that has a low surface tension will have a very low contact angle when placed on the enamel surface and thus be better suited to penetrate into the enamel porosities. The oxidizer composition should comprise hydrogen peroxide in an aqueous form (or mixed with viscosity-reducing solvents) and at a concentration between about 1% and 30% by weight (higher amounts being contemplated in situations where precise control and placement of the oxidizing composition is possible). The oxidizing composition should also have a within a range similar to that reported for the isoelectric point of tooth enamel, which is between about 3.8 and 4.7, although higher pH levels are possible with oxidizing compositions comprising ionized species capable of counteracting the influence of charged components in tooth enamel. The oxidizing composition is brushed repeatedly onto the tooth surfaces to be whitened over the period of about 7-10 minutes to provide as much full strength hydrogen peroxide at the interface over the initial treatment phase.

Step 2a Application of Oxidizing Composition to Buccal and (Optionally) Lingual Surfaces of Teeth Oxidizer Composition Example 1D Step 3—Sealing Enamel Surface Prior to Dental Prophylaxis Procedure In order to prevent dilution or removal of the oxidizing composition in or from the tooth enamel treated in accordance with Step 2 above, a water-resistant protective sealant is applied (and if solvent-based, allowed sufficient time for the carrier solvent to evaporate). The sealant composition may also comprise an additional oxidizine, agent to provide an additional reservoir of whitening active, and/or an advanced oxidation catalyst in order to promote active oxidizing species such as hydroxyl radicals (.OH) and perhydroxyl anions (—OOH) and/or a desensitizing agent to reduce or eliminate any tooth sensitivity associated with the procedure.

Step 3a Application of Sealant to Buccal and (Optionally) Lingual Surfaces of Teeth Sealant Composition

| Ingredient | Percent (w/w) |
| --- | --- |
| Ethanol 200 proof | 90.0 |
| Poly (butyl methacrylate-co-(2-dimethylaminoethyl) methacrylate-co-methyl methacrylate)* | 10.0 |

*Eudragit E100 or EPO (Evonik Rohm GmbH, Darmstadt, (Germany)

The sealant composition is applied onto the surfaces of the teeth previously contacted with the oxidizing composition and allowed to fully dry before proceeding to Step 4.

Step 4—Performance of the Dental Prophylaxis Procedure

Following the sealing process, a dental prophylaxis is performed using, standard protocols and materials. Care should be taken to avoid excessive disruption of the sealant on the buccal and lingual (if coated) surfaces of the teeth during the cleaning procedure. The dental prophylaxis is otherwise performed in a standard fashion, including polishing of the teeth with a standard prophy paste (which will remove the Sealant applied in Step 3). A final tooth shade may be taken at this time.

Step 5—Final Treatment

If time permits, Steps 2 and 3 are repeated after prophy cleanup. No further intervention is required to remove the Sealant if applied after completion of the dental prophylaxis and dismissal of the patient. The Sealant may remain in place after the patient leaves the office and will slowly erode over time. The patient may also be supplied with a home-use version of the oxidizing composition and the sealant as an option for continued improvement in tooth color.

The above steps were performed on extracted molars and premolars (n=25) obtained through orthodontists with patient consent and stored refrigerated in phosphate buffered saline (PBS) solution at pH 6.8 until use. Individual teeth were removed from the PBS solution, allowed to air dry for 60 seconds and the roots inserted, up to the cementoenamel junction into a high viscosity aqueous gel to keep the roots hydrated during the procedure. An initial tooth shade was taken using a Minolta CM504i chromameter (Konica-Minolta) and recorded. Steps 2 (total treatment time of 10 minutes) and 3 (total treatment time of 120 seconds) were performed on the extracted teeth, and a 32 minute period was allowed to elapse during, which the teeth were rinse with water every 8 minutes to simulate the rinsing process that typically occurs during the cleaning process. After the simulated cleaning process time had elapsed, the teeth were polished with a medium grit prophy paste using, a slow speed handpiece and prophy cup. Teeth were rinse with water and a final tooth shade was taken using the method described above and recorded in Table 2 below (L, a, b=Initial color readings. L*, a*, b*=final color readings).

TABLE 2

| Tooth | L | a | b | L* | a* | b* | Delta L | Delta a | Delta b | Delta E |
|---|---|---|---|---|---|---|---|---|---|---|
| 1 | 76.10 | 3.14 | 15.98 | 78.11 | 1.61 | 13.13 | 2.01 | −1.53 | −2.85 | 3.81 |
| 2 | 76.90 | 3.44 | 12.45 | 80.98 | 2.40 | 13.01 | 4.08 | −1.04 | 0.56 | 4.25 |
| 3 | 74.23 | 3.32 | 16.05 | 78.33 | 1.98 | 12.77 | 4.10 | −1.34 | −3.28 | 5.42 |
| 4 | 74.25 | 2.00 | 16.21 | 77.21 | 1.74 | 12.12 | 2.96 | −0.26 | −4.09 | 5.06 |
| 5 | 78.21 | 3.24 | 14.76 | 80.43 | 1.99 | 11.26 | 2.22 | −1.25 | −3.50 | 4.33 |
| 6 | 75.21 | 3.01 | 15.90 | 77.77 | 2.45 | 14.01 | 2.56 | −0.56 | −1.89 | 3.23 |
| 7 | 74.79 | 1.82 | 13.88 | 78.23 | 1.43 | 13.20 | 3.44 | −0.39 | −0.68 | 3.53 |
| 8 | 72.24 | 3.32 | 16.43 | 75.20 | 2.99 | 13.95 | 2.96 | −0.33 | −2.48 | 3.88 |
| 9 | 73.19 | 3.87 | 15.81 | 78.81 | 2.33 | 10.32 | 5.62 | −1.54 | −5.49 | 8.01 |
| 10 | 77.31 | 3.66 | 14.73 | 77.60 | 1.84 | 9.99 | 0.29 | −1.82 | −4.74 | 5.09 |
| 11 | 71.89 | 3.97 | 17.68 | 76.39 | 2.77 | 14.02 | 4.50 | −1.20 | −3.66 | 5.92 |
| 12 | 74.54 | 3.58 | 14.32 | 78.40 | 2.87 | 13.13 | 3.86 | −0.71 | −1.19 | 4.10 |
| 13 | 73.29 | 3.82 | 14.65 | 78.41 | 2.02 | 13.03 | 5.12 | −1.80 | −1.62 | 5.66 |
| 14 | 74.03 | 3.92 | 16.33 | 76.75 | 2.36 | 14.56 | 2.72 | −1.56 | −1.77 | 3.60 |
| 15 | 71.99 | 2.98 | 15.03 | 77.90 | 1.75 | 11.82 | 5.91 | −1.23 | −3.21 | 6.84 |
| 16 | 73.98 | 3.92 | 15.57 | 78.02 | 1.99 | 11.08 | 4.04 | −1.93 | −4.49 | 6.34 |
| 17 | 73.12 | 3.22 | 16.23 | 76.19 | 1.56 | 13.84 | 3.07 | −1.66 | −2.39 | 4.23 |
| 18 | 76.00 | 3.42 | 15.48 | 78.88 | 1.98 | 10.63 | 2.88 | −1.44 | −4.85 | 5.82 |
| 19 | 73.94 | 3.73 | 14.14 | 78.58 | 2.02 | 10.73 | 4.64 | −1.71 | −3.41 | 6.01 |
| 20 | 74.74 | 3.46 | 15.02 | 77.33 | 2.38 | 13.05 | 2.59 | −1.08 | −1.97 | 3.43 |
| 21 | 70.95 | 3.98 | 17.43 | 75.02 | 2.97 | 12.83 | 4.07 | −1.01 | −4.60 | 6.22 |
| 22 | 73.49 | 4.03 | 16.55 | 77.91 | 3.13 | 13.43 | 4.42 | −0.90 | −3.12 | 5.48 |
| 23 | 76.03 | 3.10 | 18.30 | 78.73 | 1.57 | 13.22 | 2.70 | −1.53 | −5.08 | 5.95 |
| 24 | 73.83 | 3.28 | 17.43 | 77.00 | 1.22 | 10.15 | 3.17 | −2.06 | −7.28 | 8.20 |
| 25 | 74.17 | 2.98 | 15.12 | 78.36 | 2.09 | 11.03 | 4.19 | −0.89 | −4.09 | 5.92 |
| Average | 73.94 | 3.46 | 16.03 | 77.63 | 2.06 | 11.98 | 3.79 | −1.40 | −4.04 | 5.72 |

Example 3

The following whitening method was used to demonstrate the ability of a high viscosity tooth whitening composition to remove an artificial stain from the surface of a bovine enamel substrate in vitro when light energy is use to enhance penetration.

Staining of Bovine Enamel Slabs
1. Substrates
    a. 10 mm×10 mm bovine incisor (enamel) fragments mounted in clear resin
    b. 600 grit finished surface
    c. Unsealed
2. Storage of Substrates
    a. Always store substrates at 100% relative humidity, or at 4° C. in Double Distilled $H_2O$ or Phosphate Buffered Saline solution
    b. Never allow substrates to fully dry out as surface will change, dry only as part of staining procedure and never for extended periods.
3. Staining Solution
    a. 3 g of fine ground leaf Tea
    b. 3 g of fine ground Coffee
    e. 300 ml of boiling $ddH_2O$
    d. Infuse fix 10 min with stirring (use magnetic stirrer)
    e. Filter solution through tea strainer with additional filter paper
    f. Cool to 37° C.
4. Preparation of tooth samples
    a. Labelling: Label the bovine samples on one side of the resin with permanent marker (to track the samples if using more than one)
    b. Rub the surface of the enamel with wet wipe and then grit finish is on the wet surface with orbital motion covering the whole surface for nearly 10 sec
    c. Wash the surface with water and make it dry with Kimwipe
    d. Sealing: Seal all the surfaces of the resin, excluding the enamel surface of bovine fragment (i.e., all four sides and bottom) with clear nail varnish
    e. Leave it on bench top for air drying with the enamel surface touching the bottom for 30-45 min
    f. Etching: sequential immersion in 0.2 m HCl saturated $Na_2CO_3$, 1% Phytic Acid (30 seconds each) and finally rinse with double distilled $H_2O$
    g. Make it dry with Kimwipe and then they are ready for staining
5. L*a*b Measurement
    Measurement before and after staining,
6. Staining Procedure
    a. Prepare the staining broth (Section 3) and fill a glass bottle with 200 ml of the broth
    b. Keep the samples to be stained in the broth continuously for four days
    c. Tighten the cap of the bottle to ensure that the broth is not evaporating from the bottle
    d. Gently mix the broth every day to make sure that the particles are not settling at the bottom of the bottle
    e. After staining the samples, rinse substrate with Millipore water (wipe it) and measure LAB values Samples of the stained bovine enamel slabs were contacted with a tooth whitening composition shown in Table 3.

TABLE 3

| Ingredient | Percent |
|---|---|
| Deionized water | 35.40 |
| Glycerin | 20.00 |
| Etidronic acid | 0.30 |
| Potassium stannate | 0.10 |
| Hydrogen peroxide | 12.00 |
| Carbopol 974P-NF | 2.00 |
| Sucralose | 0.30 |
| PEG-60 hydrogenated castor oil | 3.00 |
| Flavor | 1.00 |
| Ammonium Hydroxide 29% (to pH 5.0) | 1.10 |
| Total | 100.00 |

The above composition is a transparent gel having a viscosity of approximately 10,000 cps @25 deg C. and a pH of 5.0.

Figure 2:
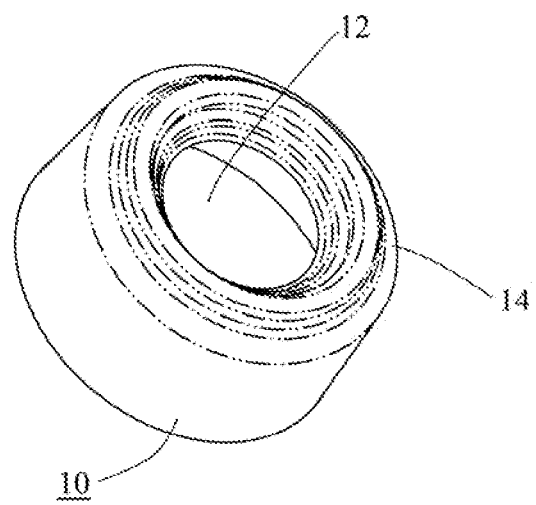
FIG. 2 is an isometric view of the over molded lens shown in FIG. 1.

The tooth whitening composition of Table 3 was brushed on to the surfaces of stained bovine enamel slabs prepared as described above. Immediately after contacting the slabs with the tooth whitening composition, light energy was applied, using a hand-held dental curing, light with a high-powered LED emitting approximately 500 mW/cm² of blue light with a peak wavelength of approximately 450 nm. The hand-held curing light used a lens cup 10 depicted schematically in FIGS. 1 and 2 as having a lens 12 over which a thermoplastic elastomer cup 14 was molded to provide a mechanism for spacing the curing light energy L (represented notionally in FIG. 1) at the same distance from the surface of the bovine slab for each sample. The over molded cup forms a small chamber that controls the positioning and movement of the gel on the tooth surface, while simultaneously emitting light energy through the lens onto the tooth surface to accelerate the penetration of the tooth whitening composition into the tooth structure.

The resulting changes in L, a and b values, together with the composite delta E change in tooth color, is shown in Table 4 below.

TABLE 4

|  | dL | da | db | dE * ab |
| --- | --- | --- | --- | --- |
| tooth 1 | 8.15 | −4.17 | −6.17 | 11.04 |
| tooth 2 | 6.91 | −3.56 | −5.71 | 9.65 |
| tooth 3 | 2.69 | −1.76 | −5.18 | 6.09 |
| tooth 4 | 5.53 | −2.89 | −2.45 | 6.71 |

As can be seen by the changes in L, a and b values, as well as the composite delta E value changes, significant tooth color changes may be effected by utilizing a high viscosity tooth whitening composition when combined with a high intensity light source adapted with a lens comprising an over molded thermoplastic elastomer spacer cup. It is anticipated that the inclusion of a light exposure step, as demonstrated in the Example, would be of significant advantage in improving the tooth whitening effect observed in Examples 1 and 2, Exposing the tooth surfaces and their surrounding soft tissue will also lead to an improvement in periodontal health through the reduction of periodontal pathogens such as black pigmented bacteria.

SUMMARY

It will be understood that the embodiments of the invention described above can be modified in myriad ways other than those specifically discussed without departing from the scope of the invention. General variations to these embodiments may include different tooth whitening compositions, light sources, methods of applying compositions and/or light, and contact and/or exposure time of tooth whitening compositions and/or light on the tooth surface.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A tooth whitening method comprising:
    applying to at least one surface of one or more teeth in place in an oral cavity an oxidizing composition comprising an oxidizing agent in an oxidizing agent fluid carrier, wherein the oxidizing agent consists of hydrogen peroxide and the oxidizing agent fluid carrier consists of water and ethanol;
    obtaining a light source that projects light energy;
    exposing one or more of the teeth surfaces with the oxidizing agent thereon to light energy using the light source;
    after the exposing step applying a separate sealant composition without an oxidizing agent directly onto one or more teeth surfaces having the oxidizing agent thereon, wherein the sealant composition comprises a water-resistant polymer dispersed or dissolved in a sealant fluid carrier, the water-resistant polymer consisting of one or more modified cellulosic polymers, silicone polymers, urethane polymers, polyamide polymers, vinyl polymers, or mixtures thereof; and
    maintaining the sealant composition in place on the teeth surfaces for a sufficient time to permit the sealant fluid carrier to evaporate and form a coating on the teeth surfaces that resists moisture contamination of the previously applied oxidizing agent.

2. The method of claim 1, wherein the step of applying the oxidizing composition is performed prior to or during the exposing step.

3. A tooth whitening method comprising:
    applying to at least one surface of one or more teeth in place in an oral cavity an oxidizing composition comprising an oxidizing agent in an oxidizing agent fluid carrier, wherein the oxidizing agent consists of hydrogen peroxide and the oxidizing agent fluid carrier consists of water and ethanol;
    obtaining a hand-held instrument with an elastomeric member comprising a chamber having a distal end and a lens molded in place at a proximal end, wherein light from a light-emitting diode is projected through the lens and chamber;
    exposing one or more of the teeth surfaces with the oxidizing agent thereon to light energy projected through the lens and chamber by moving the hand-held instrument over the tooth surface with the distal end of the elastomeric member in contact with the tooth surface;
    after the exposing step applying a separate sealant composition without an oxidizing agent directly onto one or more teeth surfaces having the oxidizing agent thereon, wherein the sealant composition comprises a water-resistant polymer dispersed or dissolved in a sealant fluid carrier, the water-resistant polymer consisting of one or more modified cellulosic polymers, silicone polymers, urethane polymers, polyamide polymers, vinyl polymers, or mixtures thereof; and
    maintaining the sealant composition in place on the teeth surfaces for a sufficient time to permit the sealant fluid carrier to evaporate and form a coating on the teeth surfaces that resists moisture contamination of the previously applied oxidizing agent.

4. The method of claim 3, wherein the elastomeric member includes a cup with a continuous wall providing an enclosed chamber with an open distal end and the lens at a closed proximal end, and the applying and exposing steps are performed by moving the open distal end of the chamber over a tooth surface to distribute oxidizing composition in the chamber over the tooth surface while exposing the tooth surface to light energy projected through the lens and oxidizing composition in the chamber.

5. The method of claim 1, wherein the sealant composition further comprises at least one of a tooth surface remineralizing agent, a tooth-desensitization agent, and one or more agents for inhibiting tooth decay, gingivitis, and/or periodontal disease.

6. The method of claim 1, wherein the sealant composition further comprises one or more colorants and/or pigments.

7. The method of claim 1, further comprising removing the coating.

8. The method of claim 1, further comprising performing a dental prophylaxis by cleaning and scaling teeth in the oral cavity, including the one or more teeth having the oxidizing agent and coating in place, in proximity to at least one of a gum line, gingival margin, and crevicular space while avoiding excessive disruption of the coating.

9. The method of claim 8, further comprising performing the following steps after performing the dental prophylaxis:
   applying another oxidizing composition comprising a fluid carrier and an oxidizing agent to one or more of the teeth having been cleaned and scaled while performing the dental prophylaxis; and
   thereafter applying another liquid sealant composition to one or more teeth having the other oxidizing agent thereon, wherein the other sealant composition comprises a fluid carrier and a water-resistant polymer, and forms a coating that resists moisture contamination of the previously applied oxidizing agent in the other oxidizing composition.

10. The method of claim 1, further comprising performing a dental prophylaxis by cleaning and scaling one or more teeth in the oral cavity prior to application of the oxidizing composition thereto.

11. The method of claim 1, further comprising removing acquired pellicle from the surfaces of the one or more teeth in place in the oral cavity before applying the oxidizing composition thereto.

12. The method of claim 11, wherein the removing step includes applying a conditioning composition including at least one tooth conditioner in a conditioner fluid carrier.

13. The method of claim 12, wherein the conditioning composition is separate from the oxidizing composition and the tooth conditioner is selected from the group consisting of phosphoric acid, hydrochloric acid, acetic acid, lactic acid, citric acid, EDTA, phytic acid, 1-hydroxyethylidene-1,1'-diphosphonic acid, and combinations thereof.

14. The method of claim 1, further comprising substantially avoiding contact of the oxidizing agent with saliva prior to the step of applying the sealant composition.

15. The method of claim 1, wherein the oxidizing composition is hydrophobic when in contact with the teeth surfaces.

16. The method of claim 1, wherein the oxidizing composition further comprises a water-resistant polymer.

17. The method of claim 1, wherein the oxidizing composition further comprises at least one component with a non-tooth whitening function.

18. The method of claim 17, wherein the component with a non-tooth whitening function is a tooth conditioner.

19. The method of claim 18, wherein the tooth conditioner is an organic acid.

20. A tooth whitening method comprising:
   applying to at least one surface of one or more teeth in place in an oral cavity an oxidizing composition comprising (i) an oxidizing agent in an oxidizing agent fluid carrier, wherein the oxidizing agent consists of hydrogen peroxide and the oxidizing agent fluid carrier consists of water and ethanol, and (ii) at least one component with a non-tooth whitening function;
   obtaining a light source that projects light energy;
   exposing one or more of the teeth surfaces with the oxidizing agent thereon to light energy using the light source;
   after the exposing step applying a separate sealant composition without an oxidizing agent directly onto one or more teeth surfaces having the oxidizing agent thereon, wherein the sealant composition comprises a water-resistant polymer dispersed or dissolved in a sealant fluid carrier, the water-resistant polymer consisting of one or more modified cellulosic polymers, silicone polymers, urethane polymers, polyamide polymers, vinyl polymers, or mixtures thereof;
   substantially avoiding contact of the oxidizing agent with saliva prior to the step of applying the sealant composition; and
   maintaining the sealant composition in place on the teeth surfaces for a sufficient time to permit the sealant fluid carrier to evaporate and form a coating on the teeth surfaces that resists moisture contamination of the previously applied oxidizing agent.

21. The method of claim 20, wherein the component with a non-tooth whitening function includes an organic acid.

* * * * *